United States Patent [19]
Fairhurst et al.

[11] Patent Number: 5,338,735
[45] Date of Patent: Aug. 16, 1994

[54] PHARMACEUTICAL COMPOUNDS

[75] Inventors: John Fairhurst, Basingstoke; David E. Tupper, Reading, both of England

[73] Assignee: Lilly Industries Limited, Basingstoke, England

[21] Appl. No.: 104,272

[22] Filed: Aug. 12, 1993

Related U.S. Application Data

[63] Continuation of Ser. No. 975,021, Nov. 12, 1992, abandoned.

[30] Foreign Application Priority Data

Nov. 18, 1991 [GB] United Kingdom ............... 9124439.2
Aug. 26, 1992 [GB] United Kingdom ............... 9218112.2

[51] Int. Cl.$^5$ .................... A61K 31/38; C07D 333/70
[52] U.S. Cl. .................... 514/233.5; 514/255; 514/324; 514/372; 514/414; 514/432; 514/443; 544/145; 544/146; 544/376; 546/202; 548/210; 548/454; 549/13; 549/28; 549/54; 549/55
[58] Field of Search .................... 549/13, 28, 54, 55; 548/210, 454; 546/202; 544/145, 146, 376; 514/233.5, 255, 324, 372, 414, 432, 443

[56] References Cited

U.S. PATENT DOCUMENTS

| | | | |
|---|---|---|---|
| 3,662,070 | 5/1972 | Thominet | 424/247 |
| 3,838,169 | 9/1974 | Thominet | 549/53 |
| 4,782,080 | 11/1988 | Witzel | 549/55 |
| 5,096,908 | 3/1992 | Gidda et al. | 514/307 |
| 5,118,680 | 6/1992 | Muller et al. | 549/55 |

FOREIGN PATENT DOCUMENTS

| | | |
|---|---|---|
| 160408 | 1/1985 | European Pat. Off. |
| 1234699 | 7/1968 | United Kingdom |
| 2193961A | 2/1988 | United Kingdom |

OTHER PUBLICATIONS

Gonzalez-Heydrich et al., J. Clin. Psychiatry, 51, 4 (1990).
Fuller et al., *Advances in Drug Research*, 17, 349 (1988).
Dreteler et al., *J. Card. Pharm.*, 14, 770 (1989).
Shepheard et al., *Eur. J. Pharm.*, 186, 267 (1990).
Lucot et al., *Pharm. Biochem. & Beh.*, 33, 627 (1989).
Othmer et al., *J. Clin. Psych.*, 48(5), 201 (1987).
Monkovic, "New Benzamide Anti-Emetics", *Drugs of the Future*, 14:1, 41–49 (1989).

*Primary Examiner*—Richard L. Raymond
*Attorney, Agent, or Firm*—MaCharri R. Vorndran-Jones

[57] ABSTRACT

Compounds of the formula:

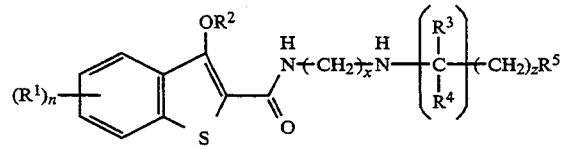

in which each $R^1$ is hydrogen, $C_{1-4}$ alkyl, $C_{1-4}$ alkoxy, halogen or nitro, and n is 0, 1, 2 or 3, $R^2$ is hydrogen, $C_{1-4}$ alkyl or $C_{2-4}$ alkenyl, $R^3$ and $R^4$ are each hydrogen, $C_{1-4}$ alkyl, optionally substituted phenyl or $C_{6-9}$ cycloalkyl optionally substituted by 1 to 4 $C_{1-4}$ alkyl groups, $R^5$ is optionally substituted phenyl, tetrahydronaphthyl, phthalimido, saccharinyl, glutaramido, $C_{6-10}$ cycloalkyl optionally substituted with 1 to 4 $C_{1-4}$ alkyl groups or a phenyl group, or $C_{4-9}$ heterosubstituted cycloalkyl optionally substituted with 1 to 4 alkyl groups, x is 1, 2 or 3, y is 0 or 1 and z is 0, 1, 2 or 3; and salts thereof.

The compounds are indicated for use in the treatment of disorders of the central nervous system.

6 Claims, No Drawings

PHARMACEUTICAL COMPOUNDS

This application is a continuation of application Ser. No. 07/975,021, filed on Nov. 12, 1992, now abandoned.

This invention relates to novel compounds and their use as pharmaceuticals.

The compounds of the invention are of the formula (I):

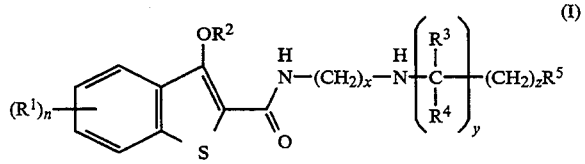

in which each $R^1$ is hydrogen, $C_{1-4}$ alkyl, $C_{1-4}$ alkoxy, halogen or nitro, and n is 0, 1, 2 or 3, $R^2$ is hydrogen, $C_{1-4}$ alkyl or $C_{2-4}$ alkenyl, $R^3$ and $R^4$ are each hydrogen, $C_{1-4}$ alkyl, optionally substituted phenyl or $C_{6-9}$ cycloalkyl optionally substituted by 1 to 4 $C_{1-4}$ alkyl groups, $R^5$ is optionally substituted phenyl, tetrahydronaphthyl, phthalimido, saccharinyl, glutaramido, $C_{6-10}$ cycloalkyl optionally substituted with 1 to 4 $C_{1-4}$ alkyl groups or a phenyl group, or $C_{4-9}$ heterosubstituted cycloalkyl optionally substituted with 1 to 4 alkyl groups, x is 1, 2 or 3, y is 0 or 1 and z is 0, 1, 2 or 3; and salts thereof.

Compounds of formula (I) have been found to possess useful biological properties, and in particular they are indicated for use in the treatment of disorders of the central nervous system.

In the above formula (I), a $C_{1-4}$ alkyl group is, for example, a methyl, ethyl, propyl, isopropyl, butyl or t.butyl group, and is preferably methyl or ethyl. A $C_{1-4}$ alkoxy group is one such alkyl group linked through oxygen to the phenyl nucleus. A halogen group is, preferably chloro, bromo or fluoro. A $C_{2-4}$ alkenyl group is preferably of the formula $-(CH_2)_nCH=CH_2$ where n is 0, 1 or 2, and a preferred example is allyl. It is preferred that a phenyl group is unsubstituted, but it can be substituted with one or more, preferably 1 to 3, substituents selected, for example, from halogen, $C_{1-4}$ alkyl, $C_{1-4}$ alkoxyl, hydroxy, nitro, cyano, amino, carboxy and carboxamido. Preferably a substituted phenyl nucleus has one or two substituents selected from halogen, $C_{1-4}$ alkyl, especially methyl or ethyl, and $C_{1-4}$ alkoxy, especially methoxy or ethoxy.

When n is 2 or 3 the substituent groups can be the same or different, but n is preferably 0. It is preferred that $R^2$ is $C_{1-4}$ alkyl, and especially preferred values of $R^1$ and $R^2$ are hydrogen and methyl, respectively.

When $R^3$, $R^4$ or $R^5$ is $C_{6-9}$ cycloalkyl it can be for example, cyclohexyl, cycloheptyl, cyclooctyl, a bridged group such as for example, bicyclooctyl or norbornyl. Preferred values are cyclohexyl, cycloheptyl and cyclooctyl. $R^5$ can in addition be a $C_{10}$ cycloalkyl group such as for example adamantyl.

When $R^3$, $R^4$ or $R^5$ is a heterosubstituted cycloalkyl group one or more carbon atoms of the cycloalkyl group is replaced by a heteroatom selected from the group consisting of oxygen, sulphur, and nitrogen. Examples include tetrahydropyranyl, tetrahydrothiopyranyl, morpholino, piperidino and piperazinyl, the group being attached via a hetero atom or by one of the carbon atoms of the cyclo nucleus. Preferably the group contains 4 or 5 carbon atoms.

Cycloalkyl groups can be substituted by 1 to 4 $C_{1-4}$ alkyl, especially methyl, groups, but are preferably unsubstituted.

With regard to the values of x, y and z, x is preferably 2, and y and z are preferably 0.

Preferred terminal amino groups are of the formula:

(1) $-NH-(CH_2)_zR^5$ where z is 0, 1 or 2, especially 0, and $R^5$ is $C_{6-9}$ cycloalkyl, or (2) $-NH-CHR^4R^5$ where $R^4$ and $R^5$ are each $C_{6-9}$ cycloalkyl.

A preferred group of compounds of formula (I) above, is one in which $R^1$ is hydrogen, $R^2$ is $C_{1-4}$ alkyl, especially methyl, $R^5$ is $C_{6-9}$ cycloalkyl, x is 2, and either (1) y is 0 and z is 0, 1 or 2, or (2) $R^3$ is hydrogen, $R^4$ is $C_{6-9}$ cycloalkyl, y is 1 and z is 0.

The compounds of the invention are useful both in their free base and acid addition salt forms. The acid addition salts are preferably the pharmaceutically acceptable, non-toxic additional salts with suitable acids, such as those with inorganic acids, for example hydrochloric, hydrobromic, nitric, sulphuric or phosphoric acids, or with organic acids, such as organic carboxylic acids, for example, oxalic, glycollic, maleic, hydroxymaleic, fumaric, malic, tartaric, citric or lactic acid, or organic sulphonic acids for example methane sulphonic, ethane sulphonic, 2-hydroxyethane sulphonic, toluene-p-sulphonic or naphthalene-2-sulphonic acid. Apart from pharmaceutically acceptable acid addition salts, other salts are also included within the scope of acid addition salts such as, for example, those with picric or oxalic acid, since they may serve as intermediates in the purification of the compounds or in the preparation of other, for example, pharmaceutically acceptable, acid addition salts, or are useful for identification, charaterisation or purification of the bases.

The invention also includes a process for producing a compound according to formula (I) above, which comprises (a) reacting a compound of the formula:

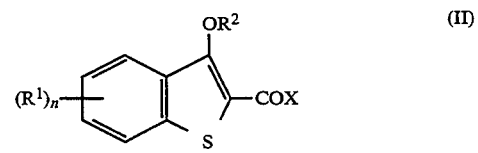

where X is a leaving group, with a compound of the formula:

$H_2N(CH_2)_xNH(CR^3R^4)_y(CH_2)_zR^5$     (III)

(b) alkylating a compound of the formula:

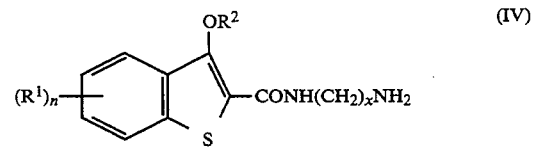

(c) reacting a compound of the formula:

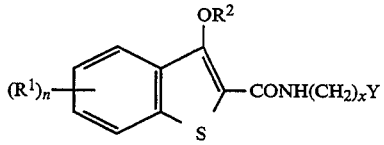

where Y is a leaving group, with a compound of the formula:

$H_2N(CR^3R^4)_y(CH_2)_zR^5$; or (d) alkylating a compound of the formula:

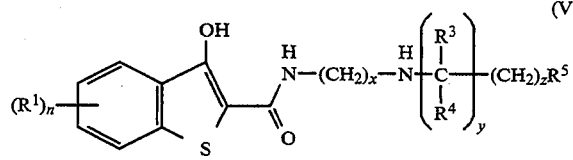

With regard to process variant (a), the reaction is preferably carried out in an organic solvent such as for example dichloromethane, chloroform, dimethylformamide or acetonitrile, and preferably at a temperature of from 0° C. to 150° C., such as at room temperature.

The intermediate of formula (II) can be prepared in situ and the leaving group X can be any of those commonly employed, such as for example imidazolide, halide and $C_{1-4}$ alkane sulphonate. The compounds are derived from known 3-hydroxbenzothiophene-2-carboxy esters, which are optionally alkylated at the 3-position, hydrolysed to give the free carboxy acid and reacted with a suitable reagent, such as for example carbonyl diimidazole to provide the compound of formula (II).

The amine reactants of formula (III) can be prepared from the appropriate alkylene diamine of formula $H_2N(CH_2)_xNH_2$ by reaction with aldehyde or ketone to provide a Schiff's base which can be reduced, catalytically, by for example, palladium or charcoal or, chemically, employing for example, sodium borohydride, to give the described amine.

With regard to process variant (b), the reaction is preferably performed in an organic solvent such as for example dichloromethane or dimethylformamide, and preferably at a temperature of from 0° C. to 150° C., such as at room temperature.

The amine reactant of formula (IV) can be prepared by reacting a compound of formula (II) with the appropriate alkylene diamine, and alkylation can be accomplished (1) by the action of the appropriate alkylating agent of formula:

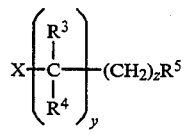

where X is, for example, halogen, or (2) by reaction with the appropriate aldehyde or ketone, followed by reduction.

With regard to process variant (c), the reaction is preferably carried out in an organic solvent such as for example dimethylformamide, dichloromethane or acetonitrile, and preferably at a temperature of from 0° C. to 150° C., for example at room temperature. The reactant of formula (V) can be prepared by reacting a compound of formula (II) with the appropriate amine of formula $H_2N(CH_2)_xY$, Y being a leaving group such as for example, halogen, especially bromo, or chloro.

With regard to process variant (d), the reaction can be carried out in an organic solvent, such as for example DMF, in the presence of a base such as sodium hydride or potassium t-butoxide, and preferably at a temperature of from 20° C. to 100° C. An alkylating agent of the formula $R^2X$ where X is for example Cl or Br is employed. The starting compound of formula (VI) can readily be prepared by one or other of the routes defined in process variants (a) to (c), or by dealkylation of a compound of formula (I).

As mentioned above, the compounds of the invention have useful central nervous system activity. The compounds are antagonists or partial agonists of the serotonin $5-HT_1$ receptor and have minimal effects upon the $\beta$-receptor. Their binding activity has been demonstrated in the test described by Wong et al, *J. Neural Transm.*, 71, 207 (1988) in which binding to the serotonin-1A receptor is measured in competition with $^3H$-8-hydroxy-2-(di-n-propylamino)tetralin, and the compounds of the invention described in the following Examples have an IC 50 in the test of less than 100 nm. Binding of the compounds of the invention to $\beta$-adrenergic receptors was also investigated in the test of Wong et al, *Biochemical Pharmacology*, 32 (7), 1287 (1983).

Because of their selective affinity for the $5-HT_{1A}$ receptor, the compounds of the present invention are indicated for use in treating a variety of conditions such as obesity, bulemia, depression, hypertension, aging, memory loss, sexual dysfunction, anxiety, schizophrenia, gastrointestinal disorders, headaches and cardiovascular disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt thereof, associated with a pharmaceutically acceptable carrier. In making the compositions of the invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propylhydroxybenzoate, talc, magnesium stearate or mineral oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions for parenteral use or as suppositories. A preferred formulation is an injection especially a sustained release formulation for intra-muscular injection. Preferably the compositions are formulated in a dosage unit form, each dosage containing from 0.5 to 100 mg, more usually 1 to 100 mg, of the active ingredient.

The following Examples illustrate the invention:

EXAMPLE 1

1. 3-Methoxy benzothiophene-2-carboxylic acid

Lithium hydroxide (5.0 g) was added portionwise to an ice-cold solution of methyl thioglycolate (8 ml) and methyl 2-nitrobenzoate (10.86 g) in dry dimethyl formamide (120 ml). The solution was stirred at 0° for 30 minutes and at room temperature for 3 hours, after which time it was poured into ice-water. The solution was acidified with concentrated hydrochloric acid and left for one hour. The product was collected by filtration and washed with water and dried. After recrystallisation from ethanol-water, methyl 3-hydroxy benzothiophene-2-caboxylate was obtained (m.p. 108°–109°).

A solution of methyl 3-hydroxy benzothiophene-2-carboxylate (10.4 g)dimethyl sulphate (6.31 g) and potassium carbonate (6.91 g) in acetone (250 ml) was refluxed overnight. The solvent was removed under vacuum and the resulting solid was dissolved in water (100 ml) and ethyl acetate (150 ml) was added. Further extraction with ethyl acetate (2×100 ml), washing the collected organics with water (2×100 ml) and drying over anhydrous magnesium sulphate gave, after removal of solvent, methyl 3-methoxy benzothiophene 2-carboxylate.

This product (8.88 g) was added to a solution of ethanol (40 ml) and water (120 ml) containing sodium hydroxide (3.2 g) and the mixture refluxed for one hour. After cooling, the solution was acidified with 5N HCl. The thick precipitate was collected and washed with water to give 3-methoxy benzothiophene-2-carboxylic acid as a slightly pink solid.

2. N-Cyclohexyl ethylene diamine

Cyclohexanone (50 g) and ethylene diamine (60 g) were mixed in ethanol (50 ml) at room temperature and allowed to stand for one hour. Meanwhile Adams catalyst (1 g) in ethanol (20 ml) was pre-reduced on a Parr apparatus at 60 p.s.i. under hydrogen for one hour. The imine solution was added to the hydrogenation flask and reduced at 60 p.s.i. for 18 hours. The catalyst was removed by filtration and the ethanol removed under vacuum. N-Cyclohexyl ethylene diamine was obtained on distillation of the crude product collecting the fraction boiling between 110°–120° C. at 20 ram.

3. N-(2-(Cyclohexylamino)ethyl)-3-methoxy-benzothiophene 2-carboxamide

To a solution of 3-methoxy benzothiophene 2-carboxylic acid (1.56 g) in dry dichloromethane (60 ml) was added carbonyl diimidazole (1.34 g) in one portion. The clear solution was stirred at room temperature for one hour. N-Cyclohexyl ethylene diamine (1.06 g) was added in one portion and the solution stirred overnight at room temperature. The solvent was removed in vacuum and the residue dissolved in water (50 ml) and ethyl acetate ( 50 ml ). Further extractions with ethyl acetate (2×50 ml), aqueous wash of the collected organic fractions and drying of the solution with anhydrous magnesium sulphate gave, after filtering, a solution which after removal of the solvent under vacuum gave a solid. A hydrochloride salt was formed ex ethanol-ether, m.p. 216°–218° C.

Similarly prepared were:

N-[2-(cyclohexylamino)ethyl]-3-methoxybenzo[b]thiophene-2-carboxamide hydrochloride 240°–242° C.

3-methoxy-N-[2-(3,3,5,5-tetramethylcyclohexylamino)ethyl]-benzo[b]thiophene-2-carboxamide 120°–122° C.

3-methoxy-N-[2-(4-tetrahydrothiopyranylamino)ethyl]-benzo[b]thiophene-2-carboxamide hydrochloride 246°–248° C.

3-methoxy-N-[2-(1,2,3,4-tetrahydro-1-naphthylamino)ethyl]-benzo[b]thiophene-2-carboxamide hydrochloride 175°–178° C.

N-[2-(cyclohexylamino)ethyl]-3-ethoxybenzo[b]thiophene-2-carboxamide 181°–182° C.

N-[2-(cyclohexylamino)ethyl]-3-methoxy-5-nitrobenzo[b]thiophene-2-carboxamide hydrochloride 220°–221° C.

N-[2-(cyclohexylamino)ethyl]-3,5-dimethoxy-benzo[b]thiophene-2-carboxamide hydrochloride 178°–180° C.

N-[2-(cyclohexylamino)ethyl]-3,7-dimethoxy-benzo[b]thiophene-2-carboxamide hydrochloride 199°–200° C.

N-[2-(cyclohexylamino)ethyl]-5-fluoro-benzo[b]thiophene-2-carboxamide hydrochloride 170°–172° C.

5-chloro-N-[2-(cyclohexylamino)ethyl]-3-methoxybenzo[b]thiophene-2-carboxamide hydrochloride 226°–228° C.

6-chloro-N-[2-(cyclohexylamino)ethyl]-3-methoxybenzo[b]thiophene-2-carboxamide oxalate 214°–215° C.

N-[2-(cyclohexylmethylamino)ethyl]-3-methoxybenzo[b]thiophene-2-carboxamide hydrochloride 141°–142° C.

N-[2-(benzylamino)ethyl]-3-methoxy-benzo[b]thiophene-2-carboxamide hydrochloride 179°–180° C.

N-[2-(dicyclohexylmethylamino)ethyl]-3-methoxybenzo[b]thiophene-2-carboxamide hydrochloride 218°–220° C.

N-[2-(diphenylmethylamino)ethyl]-3-methoxybenzo[b]thiophene-2-carboxamide 148°–150° C.

1-cyclohexyl-4(3-methoxybenzo[b]thiophene-2-carbonyl)piperazine hydrochloride 229°–232° C.

(±)-N-(1-ethyl-2-pyrrolidinylmethyl)-3-methoxybenzo[b]thiophene-2-carboxamide oxalate 123°–124° C.

(±)-6-chloro-N-(1-ethyl-2-pyrrolidinylmethyl)-3-methoxybenzo[b]thiaphene-2-carboxyamide oxalate 152°–153° C.

N-(1-piperidino-ethyl)-3-methoxy-benzo[b]thiophene-2-carboxamide oxalate 221°–222° C.

N-[2-(1-cyclohexylethylamino)ethyl]-3-methoxybenzo[b]thiophene-2-carboxamide hydrochloride 145°–152° C.

EXAMPLE 2

1. 3,5,6-Trimethoxy benzothiophene 2-carboxylic acid

Methyl 2-amino-4,5-dimethoxy benzoate (11.3 g) was added to water (25 ml) containing concentrated hydrochloric acid (11 ml) and heated until a clear solution was obtained. After cooling to −5° C. using an ice-salt bath, sodium nitrite (3.7 g) in water (25 ml) was added dropwise with stirring whilst maintaining the temperature below 5°, to give a clear reddish solution.

The diazonium salt was added portion-wise to a heated (60°–70°) solution of potassium ethyl xanthate (12.8 g) in water (25 ml) containing potassium carbonate (2.0 g). The xanthate ester product precipitated from solution as a deep red oil, and this was allowed to cool. Extraction with ether (3×100 ml), washing with water (3×50 ml), drying over magnesium sulphate and filtering, gave a red oil.

This oil was immediately treated with a solution of potassium hydroxide (13 g) in methanol (40 ml) and water (10 ml) and heated to reflux for 30 minutes. After cooling with ice-water (300 ml), the solution was made acidic by carefully adding concentrated hydrochloric acid. The precipated product was washed with water, dried under vacuum at room temperature to give 4,5-dimethoxy-2-mercapto benzoic acid.

To this product (11.0 g) in water (25 ml) and 50% sodium hydroxide (5 ml) was added chloroacetic acid (4.8 g) and the solution heated at reflux for 3 hours. After cooling, diluting with water and filtering, the solution was made acid with concentrated hydrochloric acid. The product was filtered, washed with water and dried under vacuum at room temperature to give 2-carboxymethyl thio-4,5 dimethoxy benzoic acid (11.8 g).

This was added to a solution of methanol (30 ml) containing concentrated sulphuric acid (20 g) and heated for 3 hours. The solution was poured onto ice-water, extracted with ethyl acetate, washed with water, dried and evaporated to an oil, methyl 2-carbomethoxy methyl thio-4,5-dimethoxy benzoate.

This diester (6.16 g) was dissolved in methanol (20 ml) containing sodium (0.5 g) and the solution heated at reflux for 3 hours. Dilution of the reaction with water (200 ml) and acidification with concentrated hydrochloric acid gave a solid which was collected by filtration, washed with water and dried under vacuum at room temperature, to give methyl 5,6-dimethoxy-3-hydroxy benzothiophene-2 -carboxylate.

Methylation with dimethyl sulphate, and base hydrolysis of the above product, gave 3,5,6-trimethoxy benzothiophene-2-carboxylic acid.

2. N-[2-Cyclohexylamino)ethyl]-3,5,6-trimethoxybenzo[b]thiophene-2-carboxamide hydrocloride The above compound was prepared by reaction of the intermediate of 1. above with N-cyclohexyl ethylene diamine according to the method of Example 1(3), m.p. 250°–252° C.

EXAMPLE 3

1. 2-Amino ethyl-3-methoxy-benzothiophene-2-carboxamide

3-Methoxy benzothiophene 2-carboxylic acid (6.24 g) and carbonyl diimidazole (5.8 g) were dissolved in dry dichloromethane (200 ml) and stirred at room temperature for 2 hours. The solution was then added to a solution of ethylene diamine (9.0 g) in dichloromethane (50 ml) and the solution stirred overnight. After evaporation to dryness under vacuum, the residue was partitioned between ethyl acetate and water. The organic layer was extracted several times with 2N hydrochloric acid, the aqueous layer washed with ethyl acetate and then made basic with 0.88 ammonia solution. This was extracted with ethyl acetate (3×100 ml), washed with water, dried and evaporated to dryness under vacuum, to give 2-amino ethyl-3-methoxy benzothiophene-2-carboxamide.

2. N-(2-(Cycloheptyl amino)ethyl)-3-methoxy benzothiophene-2-carboxamide

The above amine (1.5 g) and cycloheptanone (0.61 g) were dissolved in toluene (100 ml) containing a catalytic amount of p-toluene sulphonic acid and the solution refluxed under Dean-Stark conditions for 4 hours. The solution was then evaporated to dryness, redissolved in ethanol (30 ml) and reduced with sodium borohydride (2.0 g) by portionwise addition, and left overnight. Dilution with water, extraction with ethyl acetate, washing the collected organics with water and drying over magnesium sulphate gave N-(2-(cycloheptylamino) ethyl ) -3-methoxy benzothiophene-2-carboxamide.

Similarly prepared were:

N-[2-(cyclooctylamino)ethyl]-3-methoxybenzo[b]thiophene-2-carboxamide hydrochloride 170°–172° C.

N-[(bicyclo[2,2,2]octan-2-ylamino)ethyl]-3-methoxybenzo[b]thiophene-2-carboxamide 95°–97° C.

3-methoxy-N-<[trans-3-phenylbicyclo[2,2,2]octan-2-ylmethylamino]ethyl>benzo[b]thiophene-2-carboxyamide hydrochloride 190°–192° C.

EXAMPLE 4

3-Methoxy-N-<2-[N-(2-phenylethyl)amino]ethyl>-benzo[b]thiophene-2-carboxamide hydrochloride N-(2-Aminoethyl)-3-methoxybenzo[b]thiophene-2-carboxamide (1.56 g) was dissolved in dimethyl fomamide (50 ml) and triethylamine (0.63 g) added. To this stirred solution was added phenethylbromide (1.27 g) and left overnight at ambient temperature. Ice-water was added, and the product extracted with ethyl acetate (3×50 ml). Organic fractions were collected, washed with water (4×50 ml),dried, filtered to yield, after removing the solvent, a clear oil. Flash chromatography eluting with 5% methanol-dichloromethane gave 3-methoxy-N-<2-[N- (2-phenylethyl)amino]ethyl>-benzo[b]thiophene-2-carboxamide which was converted to its hydrochloride.

Similarly prepared were:

3-Methoxy-N-<2-[N-(2-phenylethyl)amino]ethyl>-benzo[b]thiophene-2-carboxamide hydrochloride 190°–191° C.

3-Methoxy-N-<2-[N-(3-phenylpropyl)amino]ethyl>-benzo[b]thiophene-2-carboxamide hydrochloride 150°–151° C.

3-Methoxy-N-<2-[N-(4-phenylbutyl)amino]ethyl>-benzo[b]thiophene-2-carboxamide hydrochloride 125°–126° C.

3-Methoxy-N-<2-[N-(3-phenoxypropyl)amino]ethyl>-benzo[b]thiophene-2-carboxamide hydrochloride 164°–166° C.

3-Methoxy-N-<[4-(2-phthalimido)butylamino)ethyl>-benzo[b]thiophene-2-carboxamide hydrochloride 182°–184° C.

3-Methoxy-N-<[3-(2-phthalimido)propylamino]e-
thyl>benzo[b]thiophene-2-carboxamide hydrochloride 220°–222° C.

N-<2-[4-(2,3-Dihydro-1,1-dioxido-3-oxo-[1,2]-benzothiazol -2-yl)burylamino]ethyl>-3-methoxy-benzo[b]thiophene-2-carboxamide hydrochloride 175°–176° C.

EXAMPLE 5

1. 2-Bromoethyl-3-methoxy benzothiophene-2-carboxamide

3-Methoxy benzothiophene-2-carboxylic acid (1.56 g) and carbonyl diimidazole (1.34 g) were dissolved in dichloromethane (50 ml) and after 1 hour, 2-bromoethylamine hydrobromide (3.07 g) and triethylamine (1.52 g) were added. The reaction was stirred overnight at room temperature. Water was added (50 ml) and 30 ml 5 N HCl, and the organic layer removed. The aqueous was washed with dichloromethane (2×20 ml) and then saturated potassium carbonate solution (2×30 ml) was used to wash the collected organic fractions. Further washing with water, drying and removal of solvent gave a solid.

Similarly prepared using 3-bromopropylamine hydrobromide was 3-bromopropyl-3-methoxy benzothiophene-2-carboxamide.

2. N-[2-(2-Norbornylamino)ethyl]-3-methoxy benzothiophene-2-carboxamide

A solution of 2-bromoethyl-3-methoxy benzothiophene-2-carboxamide (1.05 g) and 2-norbornylamine(0.42 g) in dry dimethyl formamide containing triethylamine (0.38 g) was heated under a nitrogen atmosphere at 80° C. for 8 hours. The solution was poured into water and extracted with ethyl acetate (3×50 ml), organic extracts washed with water (3×100 ml), dried and the solvent removed to give an oil which was converted to its hydrochloride to give N-[2-(2-norbornylamino) ethyl ]-3 -methoxy benzothiophene-2-carboxamide.

Similarly prepared were:
N-[2-(N-Cyclohexyl-N-methylamino)ethyl]-3-methoxybenzo[b]thiophene-2-carboxamide oxalate 187°–188° C.
N-[2-(2-Adamantylamino)ethyl]-3-methoxy-benzo[b]-thiophene-2-carboxamide hydrochloride 236°–238° C.
N-[3-(Cyclohexylamino)propyl]-3-methoxy-benzo[b]-thiophene-2-carboxamide hydrochloride 226°–227° C.
N-[3-(Exo-norborn-2-ylamino)propyl]-3-methoxy-benzo[b]thiophene-2-carboxamide hydrochloride 128°–129° C.

EXAMPLE 6

3-Propoxy benzo[b] thiophene-2-carboxylic acid

A solution of methyl 3-hydroxy benzo[b]thiophene-2-carboxylate (2.1 g) in dimethyl formamide (50 ml) was treated with potassium tert-butoxide (1.2 g) and stirred at room temperature for 30 minutes. N-Propylbromide (1 ml) was added and the solution stirred at 70° C. for 18 hours.

Ice-water was added and the solution extracted with diethyl ether (3×100 ml). The collected organic extracts were washed with 2N sodium hydroxide solution, water (3×100 ml) and dried. After filtering, solvent was removed in vacuo to leave a pink oil (2.3 g).

2N Sodium hydroxide (100 ml) was added to this oil and the solution heated to reflux for 2 hours. After cooling with ice, the solution was acidified with 5N hydrochloric acid. The precipitate was filtered, washed and dried in vacuo at room temperature to give 3-propoxy benzo[b]thiophene-2-carboxylic acid.

Similarly prepared were:
3-Butoxy benzo[b]thiophene-2-carboxylic acid 120°–122° C.
3-Methyl ethoxy benzo[b]thiophene-2-carboxylic acid 135°–137° C.

Employing the method described in Example 1, the following compounds were prepared using the above intermediates.

N-[2-(cyclohexylamino)ethyl]-3-propoxy-benzo[b]thiophene-2-carboxamide hydrochloride 172°–174° C.
N-[2-(cyclohexylamino)ethyl]-3-(methylethoxy)-benzo[b]thiophene-2-carboxamide hydrochloride 192°–194° C.
3-butoxy-N-(2-(cyclohexylamino)ethyl]-benzo[b]thiophene-2-carboxamide hydrochloride 158°–160° C.

EXAMPLE 7

N-[2-(Cyclohexylamino)ethyl]-3-hydroxy-benzo[b]thiophene-2-carboxamide oxalate To a solution of sodium ethane thiolate (prepared from ethane thiol (2.2 ml) and sodium hydride (1.5 g) ) in dimethylformamide (50 ml) stirred at room temperature, was added dropwise a solution of N-[2-(N-cyclohexyl-amino)ethyl]-3-methoxy-benzo[b]thiophene-2-carboxamide (6.0 g) in dimethylformamide (20 ml). The solution was stirred for 18 hours at room temperature, then poured into ice-water and made acidic with 2N hydrochloric acid. The precipitated product was filtered, washed repeatedly with water and dried in vacuo at room temperature. The free base produced an oxalate from ethanol M.P. 220°–222° C.

EXAMPLE 8

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 9

Capsules each containing 20 mg of medicament are made as follows:

| | |
|---|---|
| Active ingredient | 20 mg |
| Dried starch | 178 mg |
| Magnesium stearate | 2 mg |

| -continued | |
|---|---|
| Total | 200 mg |

The active ingredient, starch and magnesium stearate are passed through a sieve and filled into hard gelatin capsules in 200 mg quantities.

EXAMPLE 10

A freeze dried formulation for reconstitution into an aqueous injection is prepared from the following ingredients:

| Active ingredient | 15 mg |
|---|---|
| 0.1M Hydrochloric acid | 0.48 ml |
| Mannitol | 100 mg |
| Water | to 2 ml |

The active ingredient is suspended in water, acidified with hydrochloric acid and mannitol added, and adjusted to pH5. Water is added to 2 ml and the mixture filled into vials and then freeze dried.

EXAMPLE 11

A sustained release formulation for intra-muscular injection is prepared from the following ingredients:

| Active ingredient | 20 mg |
|---|---|
| Aluminium stearate | 2 mg |
| Soya bean oil | to 2 ml |

We claim:
1. A compound of the formula:

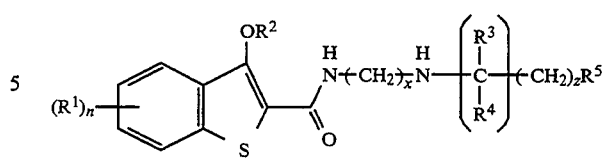

in which each $R^1$ is hydrogen, $C_{1-4}$ alkyl, $C_{1-4}$ alkoxy, halogen or nitro, and n is 0, 1, 2 or 3, $R^2$ is hydrogen, $C_{1-4}$ alkyl or $C_{2-4}$ alkenyl, $R^3$ and $R^4$ are each hydrogen, $C_{1-4}$ alkyl, optionally substituted phenyl or $C_{6-9}$ cycloalkyl optionally substituted by 1 to 4 $C_{1-4}$ alkyl groups, $R^5$ is optionally substituted phenyl, tetrahydronaphthyl, phthalimido, saccharinyl, glutaramido, $C_{6-10}$ cycloalkyl optionally substituted with 1 to 4 $C_{1-4}$ alkyl groups or a phenyl group, or $C_{4-9}$ heterosubstituted cycloalkyl optionally substituted with 1 to 4 alkyl groups, x is 1, 2 or 3, y is 0 or 1 and z is 0, 1, 2 or 3; and salts thereof.

2. A compound according to claim 1 in which y is 0, z is 0, 1 or 2 and $R^5$ is $C_{6-9}$ cycloalkyl.

3. A compound according to claim 1 in which y is 1, $R^3$ is hydrogen, $R^4$ is $C_{6-9}$ cycloalkyl and $R^5$ is $C_{6-9}$ cycloalkyl.

4. A compound according to claim 1 in which $R^1$ is hydrogen, $R^2$ is $C_{1-4}$ alkyl, $R^5$ is $C_{6-9}$ cycloalkyl, x is 2, and either (1) y is 0 and z is 0, 1 or 2, or (2) $R^3$ is hydrogen, $R^4$ is $C_{6-9}$ cycloalkyl, y is 1 and z is 0.

5. A pharmaceutical formulation which comprises a compound according to claim 1, or a pharmaceutically-acceptable salt thereof, together with a pharmaceutically-acceptable diluent or carrier therefor.

6. A method of treating a mammal including a human, suffering from or susceptible to a 5-$HT_{1A}$ related condition selected from the group consisting of obesity, bulimia, depression, hypertension, sexual dysfunction, anxiety, gastrointestinal disorders, headaches, and cardiovascular disorders, which comprises administering an effective amount of a compound according to claim 1, or a pharmaceutically-acceptable salt thereof.

* * * * *

UNITED STATES PATENT AND TRADEMARK OFFICE
CERTIFICATE OF CORRECTION

PATENT NO. : 5,338,735

DATED : August 16, 1994

INVENTOR(S) : John Fairhurst and David E. Tupper

Page 1 of 2

It is certified that error appears in the above-indentified patent and that said Letters Patent is hereby corrected as shown below:

Column 12, Line 5, delete

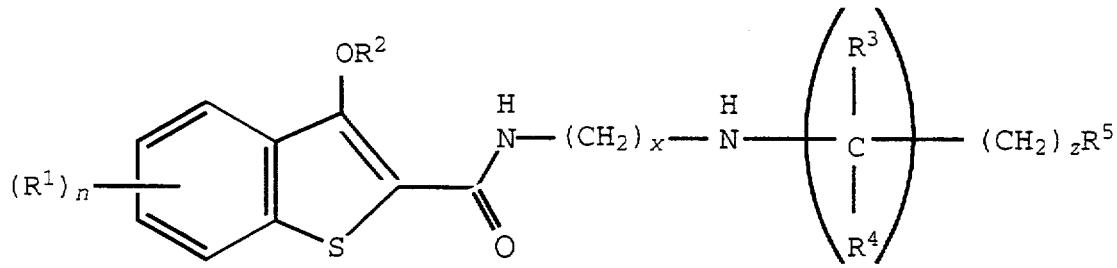

UNITED STATES PATENT AND TRADEMARK OFFICE
CERTIFICATE OF CORRECTION

PATENT NO. : 5,338,735
DATED : August 16, 1994
INVENTOR(S) : John Fairhurst and David E. Tupper It is certified that error appears in the above-indentified patent and that said Letters Patent is hereby corrected as shown below:

and insert therefore

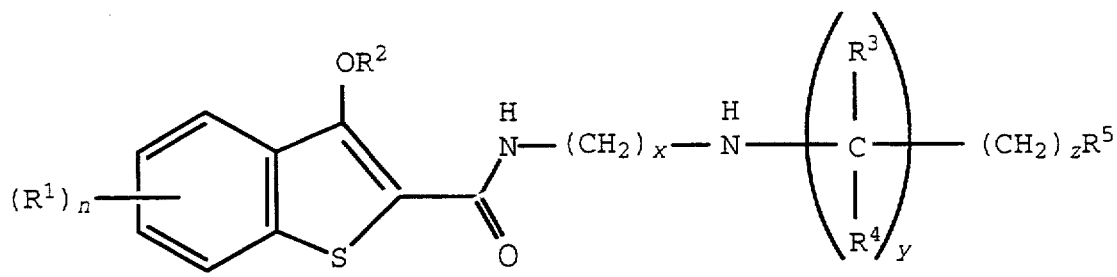

Signed and Sealed this

Twenty-first Day of March, 1995

Attest:

BRUCE LEHMAN

Attesting Officer       Commissioner of Patents and Trademarks